(12) United States Patent
Honda et al.

(10) Patent No.: US 8,390,796 B2
(45) Date of Patent: Mar. 5, 2013

(54) OIL STATE MONITORING METHOD AND OIL STATE MONITORING DEVICE

(75) Inventors: Tomomi Honda, Fukui (JP); Yoshiro Iwai, Fukui (JP); Akira Sasaki, Yokohama (JP)

(73) Assignee: National University Corporation University of Fukui, Fukui-Shi (JP)

( * ) Notice: Subject to any disclaimer, the term of this patent is extended or adjusted under 35 U.S.C. 154(b) by 0 days.

(21) Appl. No.: 13/377,942

(22) PCT Filed: Jun. 22, 2010

(86) PCT No.: PCT/JP2010/004155
§ 371 (c)(1),
(2), (4) Date: Dec. 13, 2011

(87) PCT Pub. No.: WO2010/150526
PCT Pub. Date: Dec. 29, 2010

(65) Prior Publication Data
US 2012/0086942 A1    Apr. 12, 2012

(30) Foreign Application Priority Data

Jun. 23, 2009  (JP) .................................. 2009-148911

(51) Int. Cl.
*G06K 9/74* (2006.01)
(52) U.S. Cl. ........................................................ 356/71
(58) Field of Classification Search .................... 356/71, 356/303, 326, 402, 432
See application file for complete search history.

(56) References Cited

U.S. PATENT DOCUMENTS

| | | | |
|---|---|---|---|
| 4,949,400 A * | 8/1990 | Leveen et al. | 356/420 |
| 5,141,309 A * | 8/1992 | Worwag | 356/72 |
| 5,528,036 A * | 6/1996 | Achter et al. | 250/339.12 |
| 5,586,161 A | 12/1996 | Russell et al. | |
| 5,796,472 A * | 8/1998 | Wirthlin | 356/72 |
| 7,001,451 B2 * | 2/2006 | Kim | 96/415 |
| 8,107,712 B2 * | 1/2012 | Holl | 382/135 |
| 8,194,237 B2 * | 6/2012 | Cronin et al. | 356/71 |

(Continued)

FOREIGN PATENT DOCUMENTS

| | | |
|---|---|---|
| JP | U-63-39661 | 3/1988 |
| JP | U-64-10658 | 1/1989 |

(Continued)

OTHER PUBLICATIONS

Honda et al., "Color Characterization of Membrane Patches," Society of Tribologists and Lubrication Engineers 62$^{nd}$ Annual Meeting & Exhibition, May 6-10, 2007, pp. 1-3, Philadelphia, PA, USA.

(Continued)

*Primary Examiner* — Roy M Punnoose
(74) *Attorney, Agent, or Firm* — Oliff & Berridge, PLC

(57) ABSTRACT

Disclosed are an oil state monitoring method and an oil state monitoring device which monitor the state of degradation of oil used in machinery or equipment. In monitoring the oil state by the oil state monitoring method and by the oil state monitoring device, oil used in machinery or equipment is filtered when the degradation state of the aforementioned oil is to be monitored. By means of filtration, the oil content is removed from the filter which captured contaminants that were present in oil prior to filtration. Light is projected onto the filter from which oil was removed. The projected light detects the color components of the transmitted light which penetrated the aforementioned filter.

5 Claims, 16 Drawing Sheets

U.S. PATENT DOCUMENTS

| | | | | |
|---|---|---|---|---|
| 8,203,457 | B1* | 6/2012 | Emello et al. | 340/600 |
| 8,207,508 | B2* | 6/2012 | Lawless | 250/458.1 |
| 2010/0238035 | A1* | 9/2010 | Grimshaw | 340/600 |
| 2011/0090485 | A1* | 4/2011 | Cronin et al. | 356/71 |

FOREIGN PATENT DOCUMENTS

| | | |
|---|---|---|
| JP | A-1-178865 | 7/1989 |
| JP | A-5-223729 | 8/1993 |
| JP | A-6-34541 | 2/1994 |
| JP | A-2004-84498 | 3/2004 |
| JP | A-2007-256213 | 10/2007 |
| JP | A-2007-263786 | 10/2007 |
| JP | A-2008-14652 | 1/2008 |

OTHER PUBLICATIONS

Honda, "Deterioration Diagnosis and Inspection Technology for the Lubricating Oil," Journal of the Japan Society of Precision Engineering, Mar. 5, 2009, vol. 75, No. 3, pp. 359-362 (with translation).

Honda et al., "Degradation of Lubricating Oils and Its Color," Journal of Japanese Society of Tribologists, May 15, 2008, vol. 53, No. 5, pp. 319-325 (with translation).

Aug. 3, 2010 International Search Report issued in International Application No. PCT/JP2010/004155 (with translation).

Jan. 17, 2012 Translation of Transmittal of International Preliminary Report on Patentability issued in International Application No. PCT/JP2010/004155.

Dec. 10, 2012 Supplementary European Search Report issued in Application No. 10791849.2.

Gary C. Fisher, "Polarized Light Microscopy as a Filter Debris Analysis Tool," Lubrication Engineering and/or Proceedings of the 1997 STLE Annual Meeting, vol. 54, No. 9, Sep. 1998, pp. 11-17.

A. Sasaki, "Contaminants in used oils and their problems," Proc. IMechE, vol. 220, Part J: J. Engineering Tribology, 2006, pp. 471-478.

* cited by examiner

| OIL SPECIMEN | A | B | C | D |
|---|---|---|---|---|
| IMAGE |  |  |  |  |

OIL STATE MONITORING METHOD AND OIL STATE MONITORING DEVICE

FIELD OF THE INVENTION

This invention pertains to an oil state monitoring method and an oil state monitoring device.

BACKGROUND OF THE INVENTION

Oil such as lubricant oil, hydraulic fluid, turbine oil and the like is used for various machinery or equipment. Degradation of oil causes breakdowns of or troubles with machinery and the like. Concretely, oil comes to the end of its life when oil-degradation-states reach a certain level, and using machinery and the like with such dead oil as it is will raise possibility of causing troubles with the machinery and the like. Therefore, monitoring oil degradation states is a key for preventing the troubles from occurring. Specifications related to such monitoring have been established and various technologies related to such monitoring have been proposed.

ASTM D1500 is known as one of conventional test methods for estimating life expectancy of oil by colors of oil itself. The method uses one of oil characteristics that colors of oil turn from yellow, to red, to reddish brown, and to blackish brown, and estimates oil is reaching its end of the usefulness (oil is being degraded) when a color of oil becomes almost black. However, smooth or hydraulic operations with machinery are not brought by the color characteristic of oil but brought by oil-lubricant characteristics such as oil viscosity and the like. Lubrication-property or operability-property of oil does not directly relate to colors of oil; therefore, estimating life expectancy of oil requires examination of oil for its contamination level.

Methods for examining oil contamination levels include the one according to the number of particles per each particle size-group and the one measuring weight of contaminants in oil. Representative methods of the former are NAS1638, ISO 4406, and JIS B9930, and those of the latter are ASTM D4898 and JIS 139931.

In addition, methods for estimating life expectancy of oil include ASTM D943 (commonly called as TOST) and ASTM D2272 (RPVOT test method). These days, a trend of decreasing sizes of oil tanks for machinery has been growing from a resource saving-perspective; therefore, even if oil which passed in the foregoing methods is employed for machinery, the number of cases that the oil does not work due to increase of oxidation products in the oil has been increasing. In order to solve this problem, a voltammetric method (ASTM D6810) which measures amount of antioxidant remained in oil came into use.

Besides, the following technique has been proposed. (Refer to Patent literature 1 as the example): A photometer section of a color-difference meter is directly inserted into lubricant oil in an oil tank for measuring the lubricant oil-color changes. Then, an alarm device activates when a value of the measured-oil color change exceeds the predetermined value.

Moreover, the following device, a device for simple estimation of lubricant oil-life expectancy, has been proposed. (Refer to Patent literature 2 as the example): The device for simple estimation of lubricant oil-life expectancy includes a container whose shape is designed to hold lubricant oil in a predetermined thickness. The device includes a color chart which is laid on the inside face of the container that can be seen with human eyes from the outside of the container in the through-thickness direction, and which is colored with a plurality of color-samples gradated along with lubricant oil-degradation. The device for simple estimation of lubricant oil-life expectancy judges lubricant oil-degradation levels by estimating lubricant oil-life expectancy according to relation between visible colors and invisible colors in the color chart with human eyes with the estimated-lubricant oil being held in the container.

Furthermore, the following device, a lubricant oil-degradation-monitoring device, has been proposed. (Refer to Patent literature 3 as the example): The lubricant oil-degradation-monitoring device includes a mean for sensing visible radiation which penetrates lubricant oil dividing the visible radiation into three primary colors and a mean for detecting absorbance of each of the three primary colors in the lubricant oil according to detection signals outputted from the foregoing mean for sensing the visible radiation. The lubricant oil-degradation-monitoring device reads lubricant oil-degradation levels according to the detected absorbance.

Besides, the following method, a lubricant oil-degradation level-estimation method, has been proposed. (Refer to Patent literature 4 as the example): The lubricant oil-degradation level-estimation method emits light into a lubricant oil-specimen which is put in a specimen cell. The light which penetrates the lubricant oil-specimen is divided into three light. Then, after penetrating a filter, each of the divided light is converted into electrical signals and expressed as tristimulus values of colors. Points of evaluation on the lubricant oil are given according to a chromatic coordinate gained from one of the tristimulus values and the tristimulus values and according to a constant number preset for each lubricant oil-specimen-type. A degradation and contamination state of the lubricant oil-specimen is judged according to the points of evaluation on the lubricant-oil.

In addition, a method for measuring degradation levels of lubricant oil and lubricant agents as well as a simple measurement instrument and an automatic measurement instrument related to the foregoing method have been proposed. (Refer to Patent literature 5 as the example): In Patent literature 5 as one of the examples of the method for measuring oil degradation levels, a specimen of lubricant oil or lubricant agents is applied to a flat surface-part of an instrument, which maintains almost constant roughness, for judging the oil degradation levels. Then, the applied specimen is nearly evenly leveled. The degradation level of the lubricant oil or the lubricant agents is judged according to a blackening level of the flat surface-part colored with the evenly leveled-specimen.

Several other techniques related to estimating life expectancy of oil have been introduced. (Refer to Patent literature 6 as the example.) The inventors who made the present application had also reported several research results on estimation of life expectancy of oil (Refer to Non patent literature 1).

RELATED ART DOCUMENT

Patent Literature

Patent literature 1: Japanese Unexamined Utility Model Application Publication No. 63-39661
Patent literature 2: Japanese Unexamined Utility Model Application Publication No. 64-10658
Patent literature 3: Japanese Unexamined Patent Application Publication No. H06-34541
Patent literature 4: Japanese Unexamined Patent Application Publication No. H05-223729
Patent literature 5: Japanese Unexamined Patent Application Publication No. H01-178865

Patent literature 6: Japanese Unexamined Patent Application Publication No. 2007-256213

Non-Patent Literature

Non-patent literature 1:
T. Honda, Y. Ito, K. Kodo, Y. Iwai, A. Sasaki: Color Characterization of Membrane Patches, STLE's 62nd Annual Meeting & Exhibition, Philadelphia, Pa. (USA), (2007) CD-ROM

SUMMARY OF THE INVENTION

NAS1638, ISO 4406, and JIS B9930, which are previously described as a method for judging oil contamination levels according to the number of particles per each particle size-group, are designed for measuring sizes and quantities of contaminants in oil, and are irrelevant to characteristics of the contaminants. In addition, ASTM D4898 and JIS B9931, which are previously described as a method for measuring contaminated object-weight in oil, measure total weight of contaminants in oil (100 cc), but cannot identify what type of contaminants are included in oil. In addition, even if the voltammetric method judges that sufficient amount of additive agents remain in oil, antioxidant products generated in the oil put gas turbines inoperative states in many cases.

Information that users of oil need to obtain are whether oil can be used as it is, whether purification of oil makes it possible to use the oil continuously, or whether oil already reaches its end of the life even being purified. Therefore, the aforementioned conventional methods (configurations) do not satisfy such needs of users of oil fully.

A product of oil is composed of base oil and additive agents. Using oil for machinery for a long term increases contaminants in the oil, and not only causes a negative impact on lubricity and operability of the machinery but also raises a possibility of losing properties given to the oil through consumption of additive agents in the oil. Consequently, purification of the oil which has lost its own properties such as antioxidant capabilities for attempting to use it for a long term will possibly not bring the expected results. Antioxidant capabilities of oil include a capability intrinsically owned by the base oil and a capability given by the additive agents. For example, while additive agents in oil, which are highly reactive substances, are sacrificing themselves and protecting the oil from changing the properties due to oxidation, refilling new oil for the consumed additive agents prevents damage from reaching base oil itself in the oil and can extend use duration of the oil.

The inventors of the present invention consider that proper estimation of life expectancy of oil is one of critical technological tasks to be accomplished under a current situation where depletion of oil resources may possibly occur in the near future.

The aim of the present invention is to provide a method and a device for monitoring oil states which are capable of monitoring oil states with high accuracy in order to properly estimate life expectancy of oil used in various machinery or equipment.

In monitoring degradation states of oil used in various machinery or equipment, the present invention was designed to detect color components of transmitted light being light which is emitted onto a filter, which filtered the oil and which oil contents were removed from, and which is penetrated through the filter. Oil used in various machinery or equipment in the present invention includes, for example, lubricant oil, hydraulic fluid, turbine oil and the like. The present invention also simply and collectively calls oil used for various machinery or equipment "oil".

One aspect of the present invention provides an oil state monitoring method for monitoring degradation states of oil used for machinery or equipment, characterized by comprising: a filtering step that filters the oil with a filter, a filter treatment step that removes the oil contents from the filter which filtered the oil in the filtering step and which captured contaminants which are present in the oil prior to an oil filtration, and a transmitted light-detection step that detects color components of transmitted light being light which is emitted onto the filter treated in the filter treatment step and which is penetrated through the filter.

Then, such aspect of the present invention can monitor oil degradation states according to the contaminants captured in the filter and provide the oil state monitoring method which makes it possible to monitor oil states with high accuracy in order to properly estimate life expectancy of oil used for various machinery or equipment.

The oil state monitoring method may have the transmitted light detection step include a step of detecting color components of first transmitted light which is first light that is emitted from first light source set on a side of a first face of the filter which is the side where the oil is present prior to the oil filtering in the filtering step, that is emitted onto the filter treated in the filter treatment step, and that is penetrated through the filter, on a side of a second face which is a reverse side of the first face. Such method can monitor oil degradation states according to the contaminants captured in the filter.

In addition, the oil state monitoring method may include a reflected light-detection step that detects, on the side of the first face, color components of first reflected light which is the first light reflected from the first face. Such method can monitor oil degradation states according to the contaminants captured on the first face of the filter and in the filter. The contaminants captured on the first face of the filter include those captured in areas adjacent to the first face of the filter.

Furthermore, the oil state monitoring method may have the transmitted light detection step further include a step of detecting, on the side of the first face, color components of second transmitted light which is second light that is emitted from second light source set on the side of the second face, that is emitted onto the filter treated in the filter treatment step, and that is penetrated through the filter; and may have the reflected light-detection step further include a step of detecting, on the side of the second face, color components of second reflected light which is the second light reflected from the second face.

The aforementioned method can monitor oil degradation states according to the contaminants captured on the first face of the filter, the second face of the filter, and in the filter. Thus, oil degradation states can be judged according to information obtained from a side of the first face and from a side of the second face collectively. In other words, the oil degradation states can be monitored irrespective of distribution of the contaminants in the filter. The contaminants captured on the second face of the filter include those captured in areas adjacent to the second face, in the same manner for the contaminants captured on the first face of the filter.

The other aspect of the present invention provides an oil state monitoring device for monitoring oil degradation states with a filter, which filters oil used in machinery or equipment, which captures contaminants which are present in the oil prior to an oil filtration, and which oil contents were removed from, characterized by comprising a light source that emits light emitted onto the filter set in the oil state monitoring device to monitor the oil degradation states, and a color sensor that detects color components of transmitted light which is light emitted from the light source and penetrated through the filter set in the oil state monitoring device.

Then, such aspect of the present invention can monitor oil degradation states according to the contaminants captured in the filter and provide the oil state monitoring device which makes it possible to monitor oil states with high accuracy in order to properly estimate life expectancy of oil used for various machinery or equipment.

The oil state monitoring device may have a first light source that is installed as the light source at least on a side of a first face, which is either side of the filter set in the oil state monitoring device and which is a side where the oil is present prior to the oil filtration at the filtering, and that emits first light emitted onto the filter set in the oil state monitoring device; and a first color sensor that is installed as the color sensor at least on a side of a second face which is a reverse side of the first face and that detects color components of first transmitted light which is the first light penetrated through the filter set in the oil state monitoring device. Such device can monitor oil degradation states according to the contaminants captured in the filter.

In addition, the oil state monitoring device may further include a second color sensor that is installed as the color sensor on the side of the first face and that detects color components of first reflected light which is the first light reflected from the filter set in the oil state monitoring device. Such device can monitor oil degradation states according to the contaminants captured on the first face of the filter and in the filter. The contaminants captured on the first face of the filter include those captured in areas adjacent to the first face.

Furthermore, the oil state monitoring device may further include a second light source that is installed as the light source on the side of the second face and that emits second light emitted onto the filter set in the oil state monitoring device, wherein the first color sensor further detects color components of second reflected light which is the second light reflected from the second face and the second color sensor further detects color components of second transmitted light which is the second light penetrated through the filter set in the oil state monitoring device.

The aforementioned device can monitor oil degradation states according to the contaminants captured on the first face of the filter, on the second face of the filter, and in the filter. Thus, oil degradation states can be judged according to the information obtained from a side of the first face and from a side of the second face collectively. In other words, oil degradation states can be monitored irrespective of distribution of the contaminants in the filter. The contaminants captured on the second face of the filter include those captured in areas adjacent to the second face, in the same manner for the contaminants captured on the first face of the filter.

Moreover, the aforementioned oil state monitoring device may have the first light source and the first color sensor installed not facing each other in the oil state monitoring device. Such positional relation can limit errors in detecting the color components due to distribution of intensity of the first transmitted light.

BRIEF DESCRIPTION OF THE DRAWINGS

FIG. 8 shows picture images of membrane filters which filtered the oil and which oil contents were removed from.

DESCRIPTION OF THE PREFERRED EMBODIMENTS

Details of embodiments for carrying out the present invention are explained with the figures. The present invention is not limited to the following described configurations, and may use various configurations under the same technological idea. For example, a certain unit can be omitted from the following described—each configuration.

Figure 1:
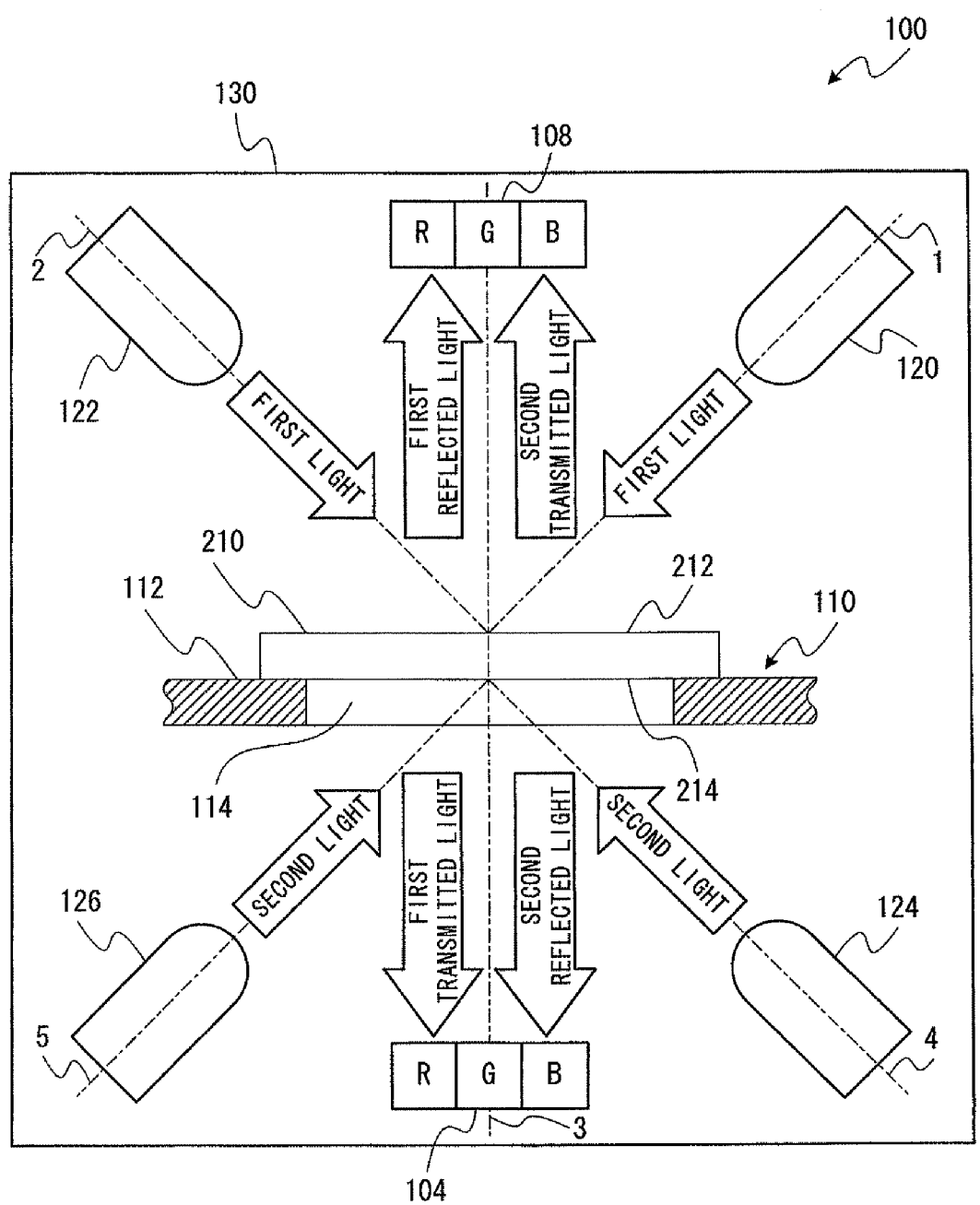
FIG. 1 shows the oil state monitoring device.
Figure 2:
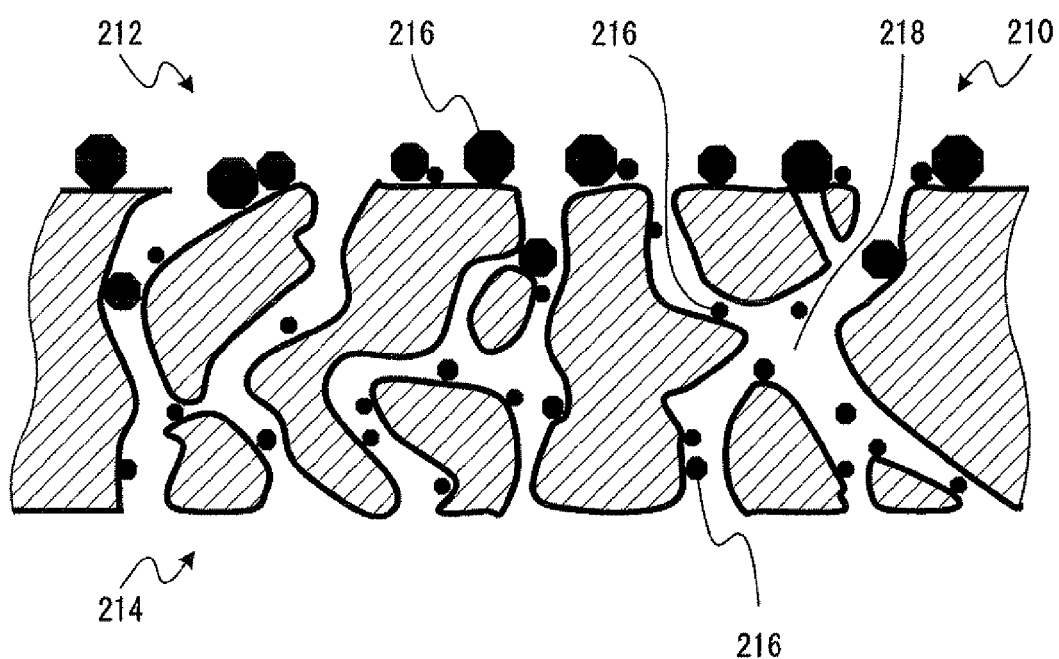
FIG. 2 explains an idea of capturing contaminants with a membrane filter.
Figure 6:
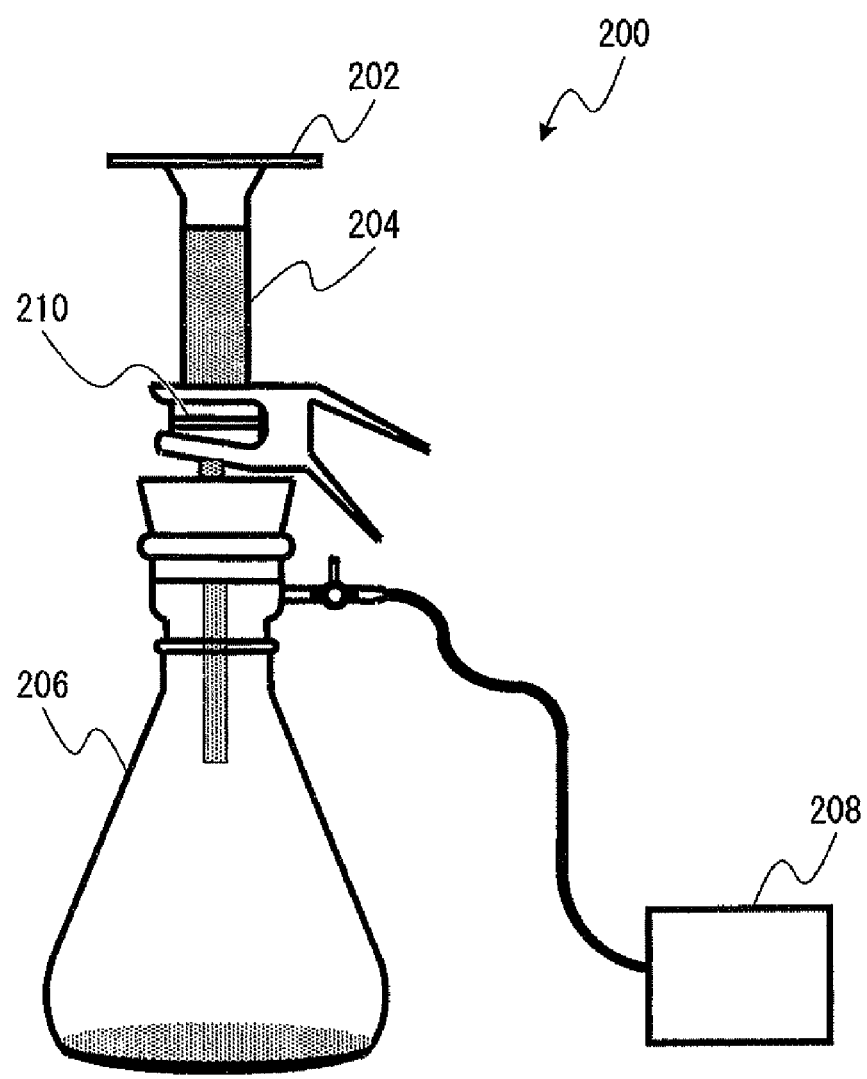
FIG. 6 shows a filtering device used for experiments.

(Oil state monitoring device) An oil state monitoring device 100 is explained with FIG. 1. The oil state monitoring device 100 is a device for monitoring oil degradation states. Oil degradation states are monitored with a membrane filter 210 which filters oil used for machinery or equipment as shown in FIG. 6, and which captures contaminants 216 which are present in the oil prior to an oil filtration as shown in FIG. 2.

The oil state monitoring device 100 includes first light sources 120, 122, and a first color sensor 104. In addition, the oil state monitoring device 100 includes second light sources 124, 126, and a second color sensor 108. Moreover, the oil state monitoring device 100 includes an installation part 110 for setting the membrane filter 210 in. The first light sources 120 and 122 are installed in the oil state monitoring device 100, specifically, on a side of a first face 212 of the membrane filter 210 set in the installation part 110, for monitoring the oil degradation states. The first light sources 120 and 122 emit first light which is emitted onto the installed membrane filter 210. The first light is visible radiation. The first face 212 is one of faces of the membrane filter 210 which is a side where oil is present prior to an oil filtration, as shown in FIG. 6 for example, in a first step of an oil monitoring method. The oil filtration is described hereinafter.

The second light sources 124 and 126 are installed on a side of a second face 214 which is a reverse side of the first face 212 of the membrane filter 210 set in the installation part 110. The second light sources 124 and 126 emit second light that is emitted onto the installed membrane filter 210. The second light is visible radiation. The first light sources 120, 122 and the second light sources 124, 126 are comprised of, for example, a white LED. The first light sources 120, 122 and the second light sources 124, 126 emit light onto predetermined areas of the membrane filter 210 set at the installation part 110. Such predetermined areas, where the first light sources 120, 122 and the second light sources 124, 126 are emitted, are described hereinafter.

A hollow space 114 is made in the installation part 110. The hollow space 114 does not block out first transmitted light, which is the first light emitted from the first light sources 120 and 122, from entering a side of the first color sensor 104; and allows the second light emitted from the second light sources 124 and 126 to reach the second face 214. The membrane filter 210 is set so that a part of the membrane filter 210, which filters oil, in other words, which captures the contaminants 216, fits in the hollow space 114.

The first color sensor 104 is installed on a side of the second face 214. The first color sensor 104 detects color components of the first transmitted light, which is the first light that is penetrated through the membrane filter 210 set at the installation part 110, in other words, which comes in the first face 212 and comes out from the second face 214. In addition, the first color sensor 104 detects color components of second reflected light which is the second light and reflects from the second face 214 of the membrane filter 210.

The second color sensor 108 is installed on a side of the first face 212. The second color sensor 108 detects color components of second transmitted light, which is the second light and is penetrated through the membrane filter 210 set at the installation part 110, in other words, which comes in the second face 214 and comes out from the first face 212. In addition, the second color sensor 108 detects color components of first reflected light which is the first light reflected from the first face 212 of the membrane filter 210.

The first color sensor 104 and the second color sensor 108 include an RGB color sensor and detects color components, dividing visible radiation in wavelengths between 380 nm and 780 nm into each color component (color signal), red (R), green (G), and blue (B). Each detected color component is indicated as a value in the 256 gradation. Each value of the color components, red (R), green (G), and blue (B) in the 256 gradation is also hereinafter called "the RGB value" as the collective term.

The first light sources 120, 122, the first color sensor 104, the second light sources 124, 126, and the second color sensor 108 are installed in the oil state monitoring device 100, being stored in a case body 130. The case body 130 includes a gate which is not illustrated in FIG. 1. A user of the oil state monitoring device 100 opens the gate, sets the membrane filter 210, which filtered the oil and received the below-described treatment, at the installation part 110 of the oil state monitoring device 100, and closes the gate. Closing the gate turns the inside of the oil state monitoring device 100, specifically, the inside of the case body 130, into a state where any light from the outside (external light) is blocked out, in other words, into a dark space.

The oil state monitoring device 100 has the first light source 120 and the first color sensor 104 not facing each other. Similarly, the oil state monitoring device 100 has the first light source 122 and the first color sensor 104 not facing each other. In other words, the first color sensor 104 is installed on a straight line 3 vertical to the first face 212 and the second face 214 of the membrane filter 210; specifically, vertical to an installation plane 112 which is a face of the installation part 110 on which the membrane filter 210 is set. The first light source 120 is installed on a straight line 1 intersecting with the line 3 at a predetermined angle, and the first light source 122 is installed on a straight line 2 intersecting with the line 3 at a predetermined angle. The angle made between the straight line 1 and the straight line 3 is predetermined to be the same (nearly the same) as that made between the straight line 2 and the straight line 3.

Similarly, the oil state monitoring device 100 has the second light source 124 and the second color sensor 108 not facing each other. In the same manner, the oil state monitoring device 100 has the second light source 126 and the second color sensor 108 not facing each other. In other words, the second color sensor 108 is installed on the straight line 3 vertical to the first face 212 and the second face 214 of the membrane filter 210; specifically, vertical to an installation plane 112 which is a face of the installation part 110 on which the membrane filter 210 is set. The second light source 124 is installed on a straight line 4 intersecting with the line 3 at a predetermined angle, and the second light source 126 is installed on a straight line 5 intersecting with the line 3 at a predetermined angle. The angle made between the straight line 4 and the straight line 3 is predetermined to be the same (nearly the same) as that made between the straight line 5 and the straight line 3.

The first light sources 120 and 122 which are installed on the side of the first face 212 and the second light sources 124 and 126 which are installed on the side of the second face 214 are arranged symmetrically to one of straight lines in the installation plane 112 of the installation part 110 or one of straight lines in planes parallel to the installation plane 112 as the axis. The first color sensor 104 and the second color sensor 108 are also arranged symmetrically to one of straight lines in the installation plane 112 of the installation part 110 or one of straight lines in planes parallel to the installation plane 112 as the axis. The straight lines in planes parallel to the installation plane 112 include, for example, straight lines in the membrane filter 210 set parallel to the installation plane 112. Such configuration makes it possible to detect the first transmitted light that passes through from the side of the first face 212 to the side of the second face 214 and the second transmitted light that passes through in the opposite way, from the side of the second face 214 to the side of the first face 212, with the first color sensor 104 and with the second color sensor 108, respectively, in the same conditions (in the same states). In addition, such configuration makes it possible to detect the first reflected light and the second reflected light with the second color sensor 108 and with the first color sensor 104, respectively, in the same conditions (in the same states).

Furthermore, the oil state monitoring device 100 includes a control device which controls execution of the hereinafter-described oil state monitoring method (estimation of life expectancy of oil) and a monitor which outputs, such as displays, predetermined information (Hereinafter, the monitor is explained as the one which displays the information as one of examples of the monitor). Illustration of parts related to the control device, the monitor and the like is omitted in FIG. 1. The control device reads programs for executing the oil state monitoring method (estimation of life expectancy of oil), and conducts various arithmetic processing. The oil state monitoring device 100 may have the control device and the like built-in. In this case, the control device and the like is a part of the oil state monitoring device 100. Moreover, the oil state monitoring device 100 and the like may include the control device and the like by connecting a machine such as a personal computer and the like through a connecting interface, which is not illustrated in FIG. 1.

(Oil state monitoring method) An oil state monitoring method is explained with FIG. 1. A first step of the oil state monitoring method is to filter oil used in machinery or equipment with a membrane filter 210. The oil filtration may use, for example, the membrane filter 210 whose diameter and hole-diameter are 25 mm and 0.8 μm, respectively. The oil filtration captures contaminants 216 which are present in the oil with the membrane filter 210 as shown in FIG. 2. The oil filtration is carried out along with predetermined specifications.

A concept of capturing the contaminants 216 is explained with FIG. 2 which shows cross section-view of the membrane filter 210. Oil and the membrane filter 210 are both insulators; therefore, oil which passes through the membrane filter 210 generates static electricity in the membrane filter 210. When the contaminants 216 are minute as oil oxidation-products of molecular size and not melted in oil, such minute contaminants 216 cannot be captured on a surface of the membrane filter 210, in other words, on a first face 212 or areas adjacent to the first face 212. However, when oil passes through the membrane filter 210, such minute contaminants 216 are stuck with the static electricity in holes 218 which are void spaces in the membrane filter 210.

In the second step, the membrane filter 210 which went through the first step is cleaned with, for example, petroleum ether to remove the oil contents. The membrane filter 210 which was cleaned and the oil content was removed from is dried through a predetermined method. Then, the membrane filter 210 which was dried is set at the oil state monitoring device 100. Specifically, a gate of the oil state monitoring device 100 is opened, the membrane filter 210 is set at an installation part 110, and the gate is closed.

Entering instructions of starting execution of the oil state monitoring method in the oil state monitoring device 100 starts actions of the below described-third step with the gate closed and subsequent steps in order. Instructions of starting execution of the oil state monitoring method are entered by a user, for example, through operation of the oil state monitoring device 100 or operation of a control device-operating part, which is not illustrated in FIG. 1.

In the third step, first light sources 120 and 122 emit first light, and the first light enters the first face 212 of the membrane filter 210 and exits from a second face 214. In other words, the first light emitted from the first light sources 120 and 122 penetrates the membrane filter 210. First transmitted light which penetrated the membrane filter 210 is detected being divided into each color component, red (R), green (G), and blue (B) with a first color sensor 104. In addition, in the third step, the first reflected light, which is the first light emitted from the first light sources 120 and 122 and reflects from the first face 212 of the membrane filter 210, is detected being divided into each color component, red (R), green (G), and blue (B), with a second color sensor 108.

In the fourth step, second light sources 124 and 126 emit second light, and the second light enters the second face 214 of the membrane filter 210 and exits from the first face 212. In other words, the second light emitted from the second light sources 124 and 126 penetrates the membrane filter 210. Second transmitted light which penetrates the membrane filter 210 is detected being divided into each color component, red (R), green (G), and blue (B), with the second color sensor 108. In addition, in the fourth step, the second reflected light, which is the second light emitted from the second light sources 124 and 126 and reflects from the second face 214 of the membrane filter 210, is detected being divided into each color component, red (R), green (G), and blue (B), with the first color sensor 104.

In the oil state monitoring method, order of the third step and the fourth may be reversed. Specifically, procedures taken in the fourth step may be followed by those in the third step. In other words, which of the step is carried out earlier than the other does not matter unless procedures in both of the steps are carried out at the same timing. For example, to cite the detection of each color component with the first color sensor 104, carrying out procedures of both of the steps at the same timing makes the first color sensor 104 fail to distinguish each color component of the first transmitted light and that of the second reflected light in the color component-detection.

Figure 7:
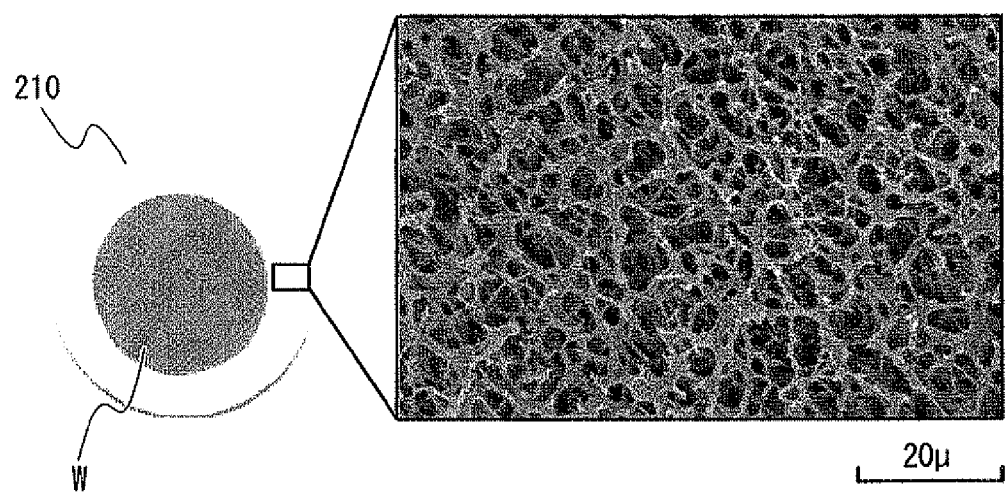
FIG. 7 shows a membrane filter.

In the third and fourth steps, the first light from the first light sources 120 and 122 and the second light from the second light sources 124 and 126 are emitted onto a predetermined area of a section W, where oil was filtered, as indicated on the left side of FIG. 7, of the first face 212 of the membrane filter 210, and that of the second face 214 of the membrane filter 210, respectively. The first light and the second light are emitted onto, for example, a predetermined large area of the section W, where oil was filtered; specifically, most of the area of the section W where oil was filtered; in other words, nearly whole area of the section W where oil was filtered.

Figure 3:
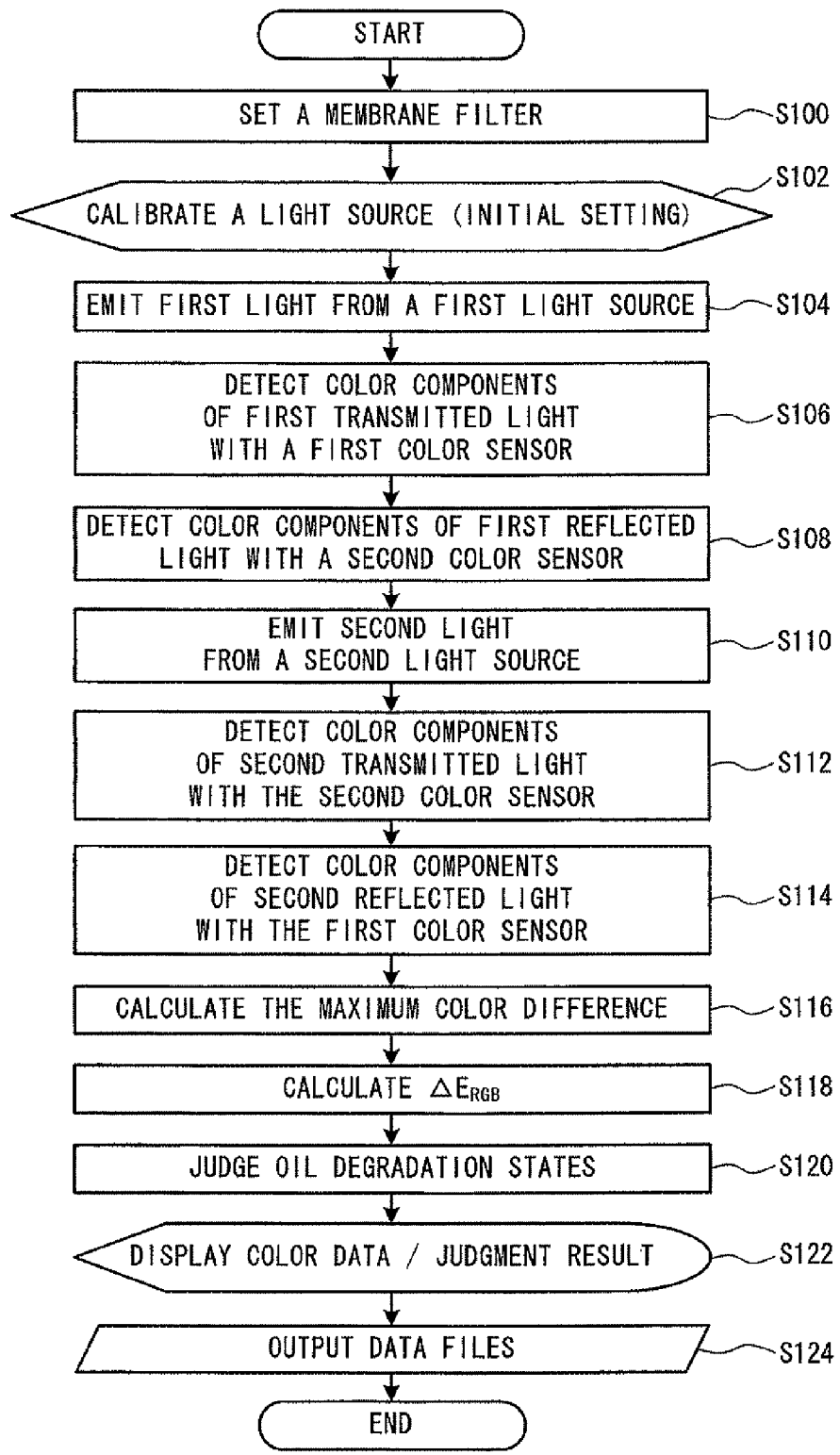
FIG. 3 is a flowchart on estimation of life expectancy of oil.

(Estimation of life expectancy of oil) Estimation of Fife expectancy of oil is explained with FIG. 3. Life expectancy of oil is estimated according to information collected through the above mentioned-oil state monitoring method; that is to say, according to each color component detected with the first color sensor 104 and the second color sensor 108. Descriptions in a flowchart for estimating life expectancy of oil include procedures corresponding to those from the first step through the fourth step of the oil state monitoring method as previously described. Therefore, the following explanation on estimation of life expectancy of oil with FIG. 3 clearly describes which part of procedures in the flowchart corresponds to the third step and the fourth step, but omits details on procedures of the foregoing steps. The procedures described in the flowchart are controlled with a control device.

The control device which is given instructions of starting the previously described procedures in the second step detects that the membrane filter 210 is set at the installation part 110 with a predetermined sensor (S100). Then, the control device calibrates; namely, initializes the first light sources 120, 122; the second light sources 124, 126; the first color sensor 104; and the second color sensor 108 (S102). That is, S102 makes the control device ready for performing its self-diagnostic-function.

Concretely, states of the first light sources 120, 122 and the second light sources 124, 126, such as luminance or luminous intensity thereof, are detected with the predetermined sensor in S102 for judging whether the detected states reach a predetermined level. In case the detected states are short of the predetermined level, states of the first light sources 120, 122 and the second light sources 124, 126 are adjusted, and the control device memorizes the states after the adjustment. In addition, states of the first color sensor 104 and the second color sensor 108 are adjusted according to predetermined standard values, and the control device memorizes the states after the adjustment. In other words, each of the first light sources 120, 122; the second light sources 124, 126; the first color sensor 104; and the second color sensor 108, which are adjusted by the self-diagnostic-function, is set in the state after the adjustment.

Then, the control device controls each procedure from S104 through S108 and that from S110 through S114. The procedures from S104 through S108 correspond to the third step in the oil state monitoring method, and the procedures from S110 through S114 correspond to the fourth step in the oil state monitoring method. Each of the procedure is previously described; therefore, details on the procedures are omitted.

In S116, the control device calculates the maximum color difference of the first transmitted light, that of the second transmitted light, that of the first reflected light, and that of the second reflected light, using each color component (the RGB value) of the first transmitted light and that of the second reflected light which are detected with the first color sensor 104, and each color component (the RGB value) of the second transmitted light and that of the first reflected light which are detected with the second color sensor 108.

The maximum color difference is a gap between the greatest value and the least value in the RGB values, and it is known that nature of contaminants can be roughly classified by the maximum color differences. This point is proposed in the previously described Non-patent literature 1. When the maximum color difference is big, amount of oxidation products, such as sludge soluble in toluene in the contaminants, is large, and the color of the membrane filter 210 which filtered the oil turns into brownish. When the maximum color difference is small, the color of the membrane filter 210 turns into blackish or whitish. When the color of the membrane filter 210 turns into blackish, a large amount of powders by abrasion or alien substances insoluble in toluene are mixed in the oil. On the contrary, turning the color of the membrane filter 210 into whitish indicates the oil is a pure one whose degradation has not taken place.

To cite the first transmitted light as the example, when the R value, the G value, and the B value of the first transmitted light is 235, 219, and 190, respectively, the difference between the R value and the G value (The value is the absolute figure. The figures hereinafter are also absolute figures), the difference between the R value and the B value, and the difference between the G value and B value are 16, 45, and 29, respectively. Then, the maximum color difference is 45. In other words, the control device obtains 45 as a result of the calculation of the maximum color difference in the first transmitted light. The maximum color differences in the other light such as the second transmitted light are calculated in the same manner; therefore, explanation (citing examples) on calculations of the maximum differences in the other light is omitted.

After carrying out procedures in S116, the control device calculates $\Delta E_{RGB}$(S118). A color of the membrane filter 210 which filtered the oil becomes darker through increase of the oil impurity level, and eventually turns to be black (0,0,0). Based on this, a distance between two colors, black (0,0,0) and a color of a membrane filter 210 is defined to be $\Delta E_{RGB}$. When a color of the membrane filter 210 is white (255,255, 255), $\Delta E_{RGB}$ becomes its maximum value of 441.67. When a color of the membrane filter 210 gets darker and eventually becomes black (0,0,0), $\Delta E_{RGB}$ indicates its minimum value of 0.

Figure 4:
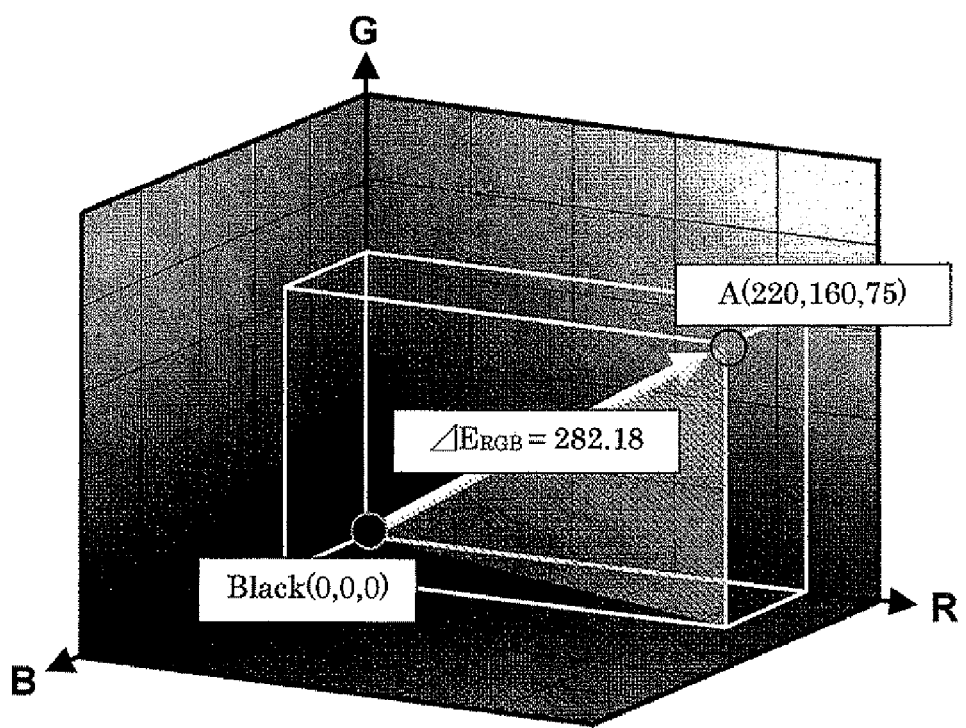
FIG. 4 explains $\Delta E_{RGB}$.
Figure 5:
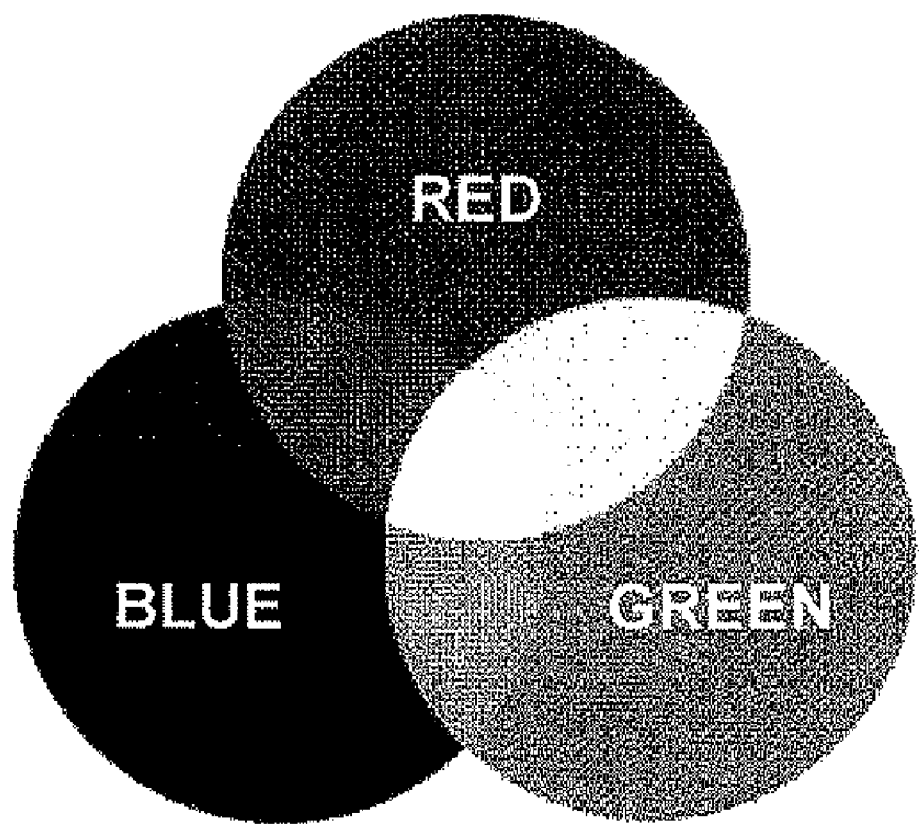
FIG. 5 shows an RGB color model.

As the example, FIG. 4 assumes the ROB-three dimensional coordinate including a point A whose position is indicated as (220,160,75). Calculation of $\Delta E_{RGB}$ of this case obtains a value indicated as (1) with the Formula 1. The inventors consider $\Delta E_{RGB}$ to be a magnitude of a vector in the RGB-three dimensional coordinate and to express chromogenic property of the membrane filter 210 in the RGB color expression system, taking account of additive mixture of colors of an ROB color model as shown in FIG. 5.

[Formula 1]

$$\Delta E_{RGB}\sqrt{R^2+G^2+B^2}=\sqrt{220^2+160^2+75^2}=282.18 \quad (1)$$

In S118, the control device calculates $\Delta E_{RGB}$ of the first transmitted light, that of the second transmitted light, that of the first reflected light, and that of the second reflected light; using each color component (the RGB values) of the first transmitted light, that of the second transmitted light, that of the first reflected light, and that of the second reflected light, respectively, in the same manner of S116. Relation between each color component of oil-oxidation products is expressed as R value>/=G value>/=B value.

After carrying out procedures in S118, the control device judges the oil degradation states according to the calculation results obtained in S116 and S118 (S120). In S120, the control device judges the oil degradation states using the maximum color difference of the first transmitted light, that of the second transmitted light, that of the first reflected light, and that of the second reflected light obtained in S116; and $\Delta E_{RGB}$ of the first transmitted light and that of the other lights obtained in S118, collectively. Then, the control device displays the color-data and the judgment result on a monitor (S122). Specifically, the control device displays, on the monitor, color data of oil (the filtered oil) whose life expectancy is to be estimated and information described as: "The oil is at the end of its life and should be replaced with new oil.", "The oil is continuously usable but partial replacement of the oil (X1%) is required.", "The oil is continuously usable but partial replacement of the oil (X2%) is required." or "The oil is continuously usable.". The color data displayed on the monitor are the RGB values and color parameters which can be converted from the RGB values. The control device displays the color parameters on the monitor, for example, the maximum color differences, $\Delta E_{RGB}$, HLS (Hue, Lightness, and Saturation)-values, or color differences in L*a*b*-color space (CIE1976) and the like. The term "X1" in "The oil is continuously usable but partial replacement of the oil (X1%) is required." and the term "X2" in "The oil is continuously usable but partial replacement of the oil (X2%) is required." mean a percentage of the oil to be replaced with new oil; thus, the term expresses a percentage of the oil to be replaced with new oil, using a certain number within a range from 1 through 99. Relation between "X1" and "X2" is expressed as "X2>X1". Replacement of the oil means to replace the whole oil with new one, and partial replacement of the oil means to drain the oil partially and the drained oil is replaced with an equal amount of new oil. In other words, partial replacement of oil means addition of oil.

Procedures in S120 are explained by citing the judgment criteria. For example, in case of oxidation degraded-turbine oil, a threshold value for judging "The oil is continuously usable." or "The oil is continuously usable but partial replacement of the oil (X1%) is required." is approximately 30 in the maximum color difference; specifically, a value within a range between 20 and 30 in the maximum color difference, and approximately 410 in $\Delta E_{RGB}$. The judgment by the control device is made according to each threshold value which is set as just described above. The threshold values are determined with consideration for various circumstances. In the same manner, a threshold value for judging "The oil is continuously usable but partial replacement of the oil (X2%) is required." or "Replacement of oil is required." is set to be; for example, approximately 50 in the maximum color difference and approximately 360 in $\Delta E_{RGB}$. An example of how to use data on the maximum color differences of the first transmitted light and the other light obtained in S116 and data on $\Delta E_{RGB}$ of the first transmitted light and the other light obtained in S118 is described as follows. The maximum color difference and $\Delta E_{RGB}$ of the first reflected light, the maximum color difference and $\Delta E_{RGB}$ of the second reflected light, an average of the maximum color difference of the first transmitted light and that of the second transmitted light, and an average of $\Delta E_{RGB}$ of the first transmitted light and that of the second transmitted light are collectively used for the judgment.

Furthermore, the control device outputs files including data on the judgment results which were displayed on the screen in S122 (S124). The output files are stored in a predetermined storage medium such as a storage unit equipped in the control device. Then, the control device ends the procedures for estimating life expectancy of oil.

(Example) An experiment was carried out for verifying effectiveness of the oil state monitoring device and method according to the above mentioned embodiments. Results of the experiment are explained as follows.

(Oil specimen) Oil-specimens were made of turbine oil which was cleaned after being actually used in a gas turbine in a power station. Specifically, major fragments in the turbine oil were removed, and specific amount of the cleaned oil was added to autoxidation-degraded-oil. The autoxidation-degraded-oil is oil made by autoxidizing the cleaned oil. Four types of the oil specimens A, B, C, and D were prepared, and details on the oil specimens are described in Table 1.

TABLE 1

| | Oil specimen |
|---|---|
| A | Autoxidation degraded oil (100%) |
| B | Autoxidation degraded oil (40%) + Cleaned oil (60%) |
| C | Autoxidation degraded oil (20%) + Cleaned oil (80%) |
| D | Cleaned oil (100%) |

(Filtering device and method) A filtering device 200 used in the experiment is explained with FIG. 6. The filtering device 200 includes a dust proofing cover 202, a cylinder 204, a flask 206, and a vacuum pump 208. A membrane filter 210 (produced by ADVANTEC MFS, INC., Product code: C080A025A), which is made of cellulose acetate and whose diameter is 25 mm and hole diameter is 0.8 μm, was installed at a position between the cylinder 204 and the flask 206. The oil specimen-filtering was carried out by injecting 25 ml of the oil specimen in the cylinder 204 and reducing a pressure in the flask 206 with the vacuum pump 208. A magnified image on the right of FIG. 7 shows a state of the membrane filter 210 used for the oil specimen-filtering.

Halftone dotted areas of the filtering device 200 in FIG. 6 designate the oil specimen. Specifically, in FIG. 6, the halftone dotted area above the membrane filter 210 designates the oil specimen before being filtered and those below the membrane filter 210 designates the oil specimen after being filtered.

(Method for measuring Reflectance and Transmittance) The membrane filter 210 after filtering the oil, as shown on the left side of FIG. 7, was cleaned with petroleum ether, and dried after the oil contents were removed. (Hereinafter, the foregoing membrane filter is also called 'the membrane filter 210 after oil content-removal'). Then, reflectance and transmittance of the membrane filter 210 after oil content-removal were measured. Specifically, reflection and transmittance in a section W where the oil specimen was filtered were measured. The reflection and transmittance were measured with an ultraviolet-visible spectrophotometer manufactured by Hitachi High-Technologies Corporation (Model name: U4100).

The measurement of reflectance is explained as follows. An unused membrane filter 210 was inserted in a holder on a reference-side as well as in a holder on a test sample-side, and the baseline was measured. Then, the membrane filter 210 after oil content-removal was inserted in the holder on the test sample-side, and the reflectance was measured under conditions described in Table 2. The reflectance was obtained with a formula, Reflectance=IR/10, by making the reflectance intensity on the reference-side 10 and the one on the test sample-side IR.

TABLE 2

| Photometric method | | Double beam-direct ratio-photometric system |
|---|---|---|
| Wavelength range | | 190 nm-2600 nm |
| Sampling interval | | 0.5 nm |
| Light source | UV | Deuterium lamp |
| | Visible/Near-infrared | 50 W halogen lamp |
| Power source switching point | | 340 nm |
| Detector | UV/Visible | Photomultiplier |
| | Near-infrared | Cooling type PbS |
| Detector switching point | | 850 nm |
| Scanning speed | UV/Visible | 120 nm/min. |
| | Near-infrared | 300 nm/min. |
| Slit width | UV/Visible | 2.0 nm |
| | Near-infrared | Automation |

The measurement of transmittance is explained as follows. An unused membrane filter 210 was inserted in the holder on the reference-side as well as in the holder on the test sample-side, and the baseline was measured. Then, the membrane filter 210 after oil content-removal was inserted in the holder on the test sample-side, and the transmittance was measured under conditions described in Table 2. The transmittance was obtained with a formula, Transmittance=IT/10, by making the transmittance intensity on the reference-side 10 and the one on the test sample-side IT.

As the measurement-comparison example, transmittance of the oil; namely, transmittance of the oil itself was measured. Specifically, an empty liquid cell made of quartz was inserted in the holder on the reference-side as well as in the holder on the test sample-side, and the baseline was measured in the same manner of the aforementioned-measurement. Then, each oil specimen A, B, C, and D was put in the empty liquid cell on the test sample-side, and transmittance of each oil specimen was measured under the conditions described in Table 2. The transmittance was obtained with a formula, Transmittance=IT/10, by making the transmittance intensity on the reference-side 10 and the one on the test sample-side IT.

Figure 8:
Figure 8:
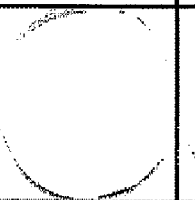
Figure 8:
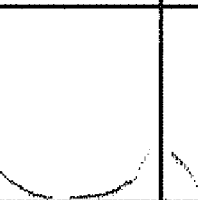
Figure 8:
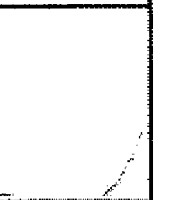

(Experiment result) As for the membrane filter 210 after oil content-removal and color parameters, colors of the membrane filter 210 became lighter as amount of the added cleaned oil increased, as is obvious in images of the membrane filter 210 in FIG. 8.

Figure 9:
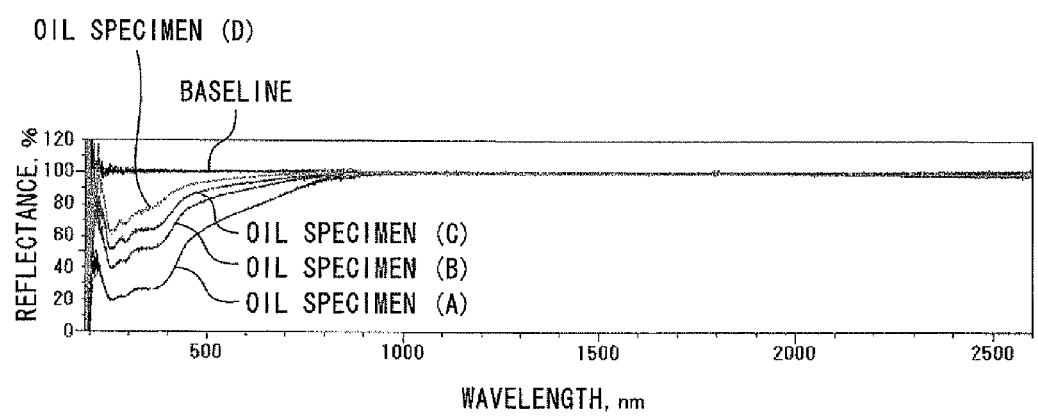
FIG. 9 is a result of experiments on reflectance of the membrane filters which filtered the oil and which oil contents were removed from, and shows the reflectance change in wavelengths between 190 nm and 2600 nm.
Figure 10:
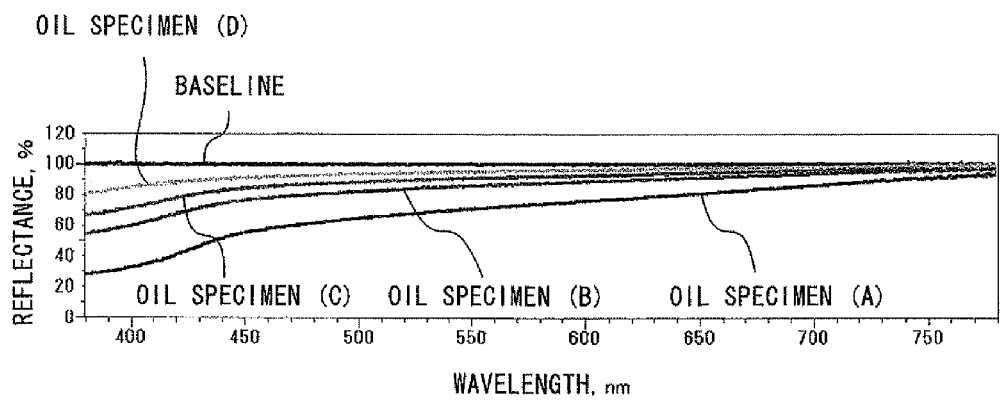
FIG. 10 is a chart which enlarged visible radiation-range-data in FIG. 9.
Figure 11:
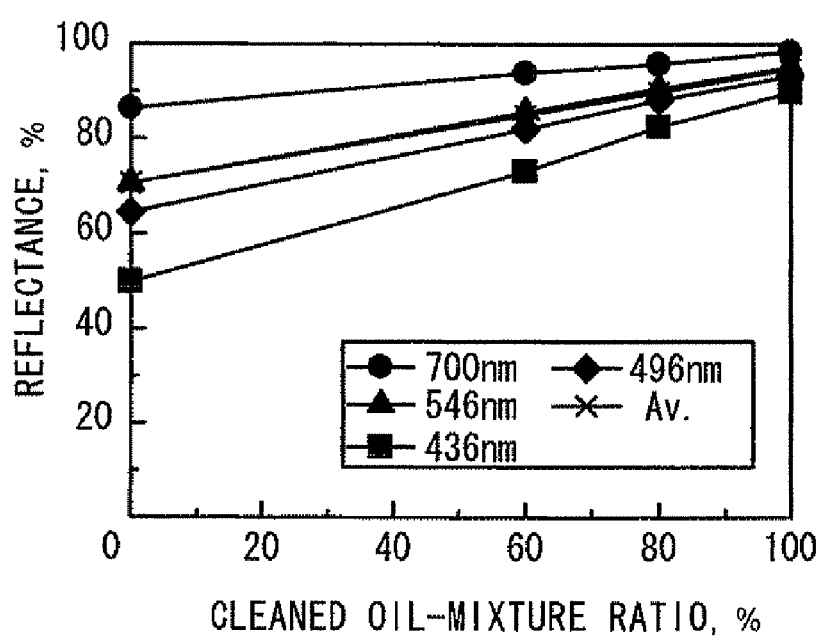
FIG. 11 is a result of experiments on reflectance of the membrane filters which filtered the oil and which the oil contents were removed from, and shows the reflectance by each wavelength.

Reflectance of the membrane filter 210 after oil content-removal is explained with FIG. 9-FIG. 11 and Table 3. FIG. 10 shows data in the visible radiation which falls within the wavelength range of 380 nm to 780 nm. Table 3 shows data of reflectance in each wavelength corresponding to data in FIG. 11. Reflectance of the membrane filter 210 after oil content-removal increased as amount of the added cleaned oil increased. Particularly, a change of reflectance of the blue color-wavelength was significant, and the reflectance increased by approximately 40%. On the other hand, transmittance of the oil as shown in Table 4 slightly increased as amount of the added cleaned oil increased, but the transmittance increase-rate was less than 1%.

TABLE 3

| Oil specimen | 700 nm % R | 546 nm % R | 436 nm % R | 496 nm % R | Av. % R |
|---|---|---|---|---|---|
| A | 86.4 | 70.7 | 49.9 | 64.5 | 70.7 |
| B | 94 | 85.8 | 73.2 | 82.1 | 85.1 |
| C | 95.9 | 90.8 | 82.6 | 88.3 | 90 |
| D | 98.5 | 95.3 | 89.9 | 93.3 | 94.9 |

TABLE 4

| Oil specimen | 700 nm % T | 546 nm % T | 436 nm % T | 496 nm % T | Av. % T |
|---|---|---|---|---|---|
| A | 103.5 | 72.4 | 8.1 | 35.5 | 67.1 |
| B | 103.7 | 72.9 | 8.3 | 35.9 | 67.2 |
| C | 103.5 | 73 | 8.4 | 36.1 | 67.4 |
| D | 103.8 | 73.2 | 8.4 | 36.2 | 67.5 |

Figure 12:
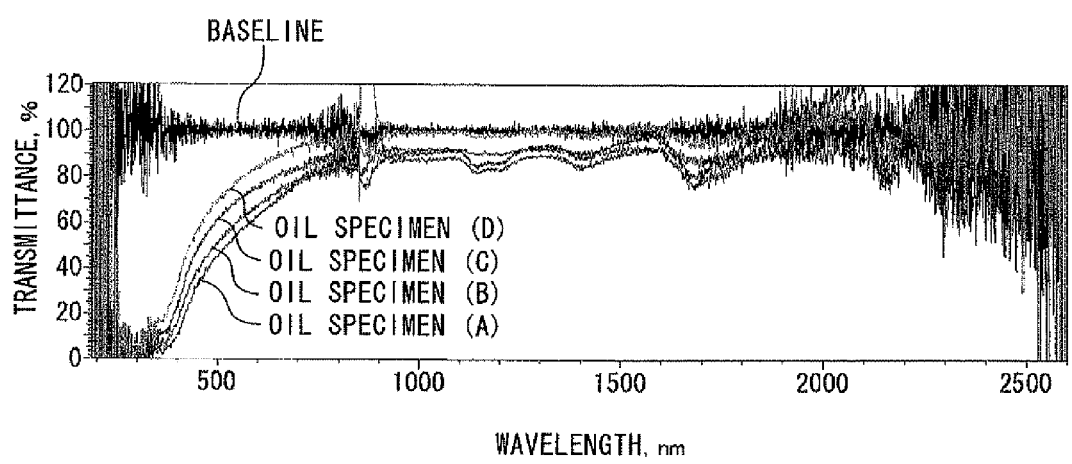
FIG. 12 is a result of experiments on transmittance of the membrane filters which filtered the oil and which the oil contents were removed from, and shows the transmittance change in wavelengths between 190 nm and 2600 nm.
Figure 13:
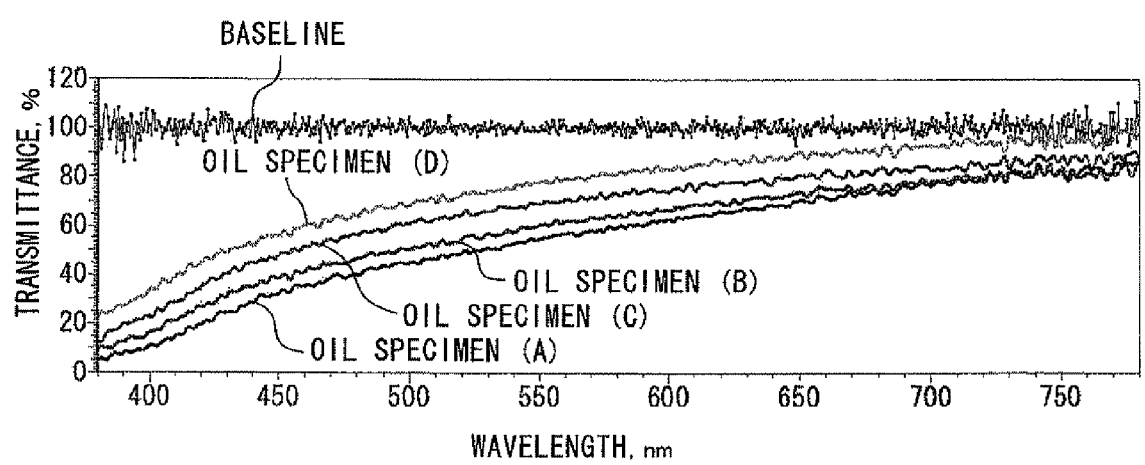
FIG. 13 is a chart which enlarged visible radiation-range-data in FIG. 12.
Figure 14:
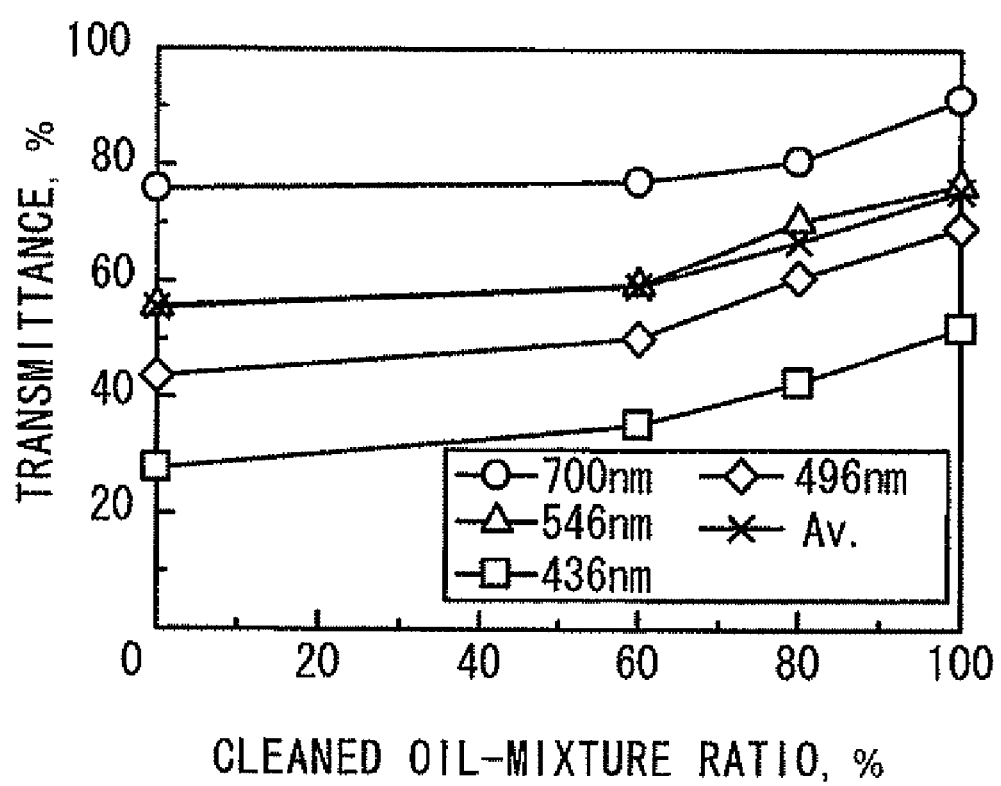
FIG. 14 is a result of experiments on transmittance of the membrane filters which filtered the oil and which the oil contents were removed from, and shows the transmittance by each wavelength.

Transmittance of the membrane filter 210 after oil content-removal is explained with FIG. 12-FIG. 14 and Table 5. Table 5 shows data of the transmittance in each wavelength corresponding to FIG. 14. The transmittance decreased, as colors of the membrane filter 210 after oil content-removal became darker, in the visible radiation which lies between 380 nm and 780 nm in the wavelength. In common with the results about the reflectance, a significant difference was found in the transmittance of the membrane filter 210 after oil content-removal even between the oil specimen C and the oil specimen D, whose colors were light, as shown in FIG. 8, and which did not show a significant difference in the ROB values.

TABLE 5

| Oil specimen | P-700 nm % T | P-546 nm % T | P-436 nm % T | P-496 nm % T | P-Av. % T |
|---|---|---|---|---|---|
| A | 75.8 | 55.6 | 27.7 | 43.6 | 55.4 |
| B | 77.1 | 59.4 | 35.3 | 50.2 | 59.2 |
| C | 80.7 | 70.3 | 42.6 | 60.7 | 66.9 |
| D | 91.3 | 76.5 | 51.9 | 69.2 | 75.5 |

The above described results showed that slight color differences in the membrane filter 210 after oil content-removal, such as light color differences between the membrane filter after oil content-removal which filtered the oil specimen C and the membrane filter after oil content-removal which filtered the oil specimen D, can be also judged with high sensitivity. Then, elements based on transmitted light which is penetrated through the membrane filter 210, specifically, the maximum color difference and $\Delta E_{RGB}$ of the first transmitted light used in the oil state monitoring of the embodiment of the present invention, are effective parameters for judging the oil degradation states. The conclusion also applies to the second transmitted light.

Figure 15:
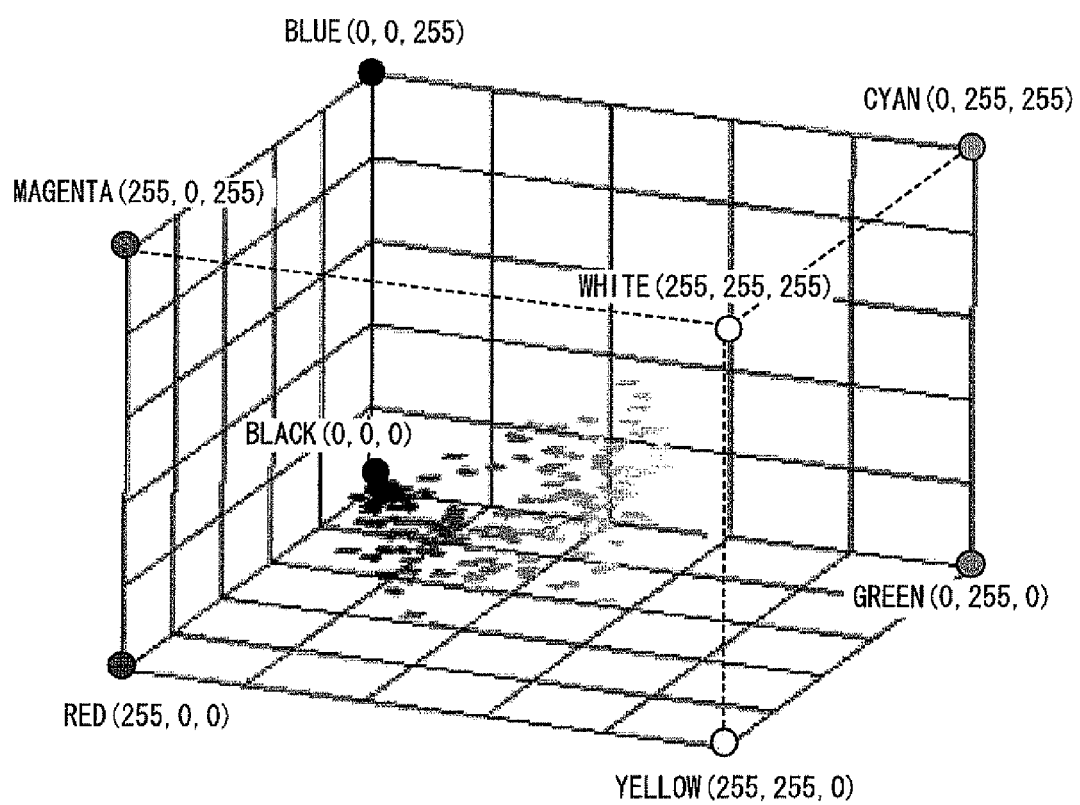
FIG. 15 is a distribution map showing contaminant-colors in three dimensions.
Figure 16:
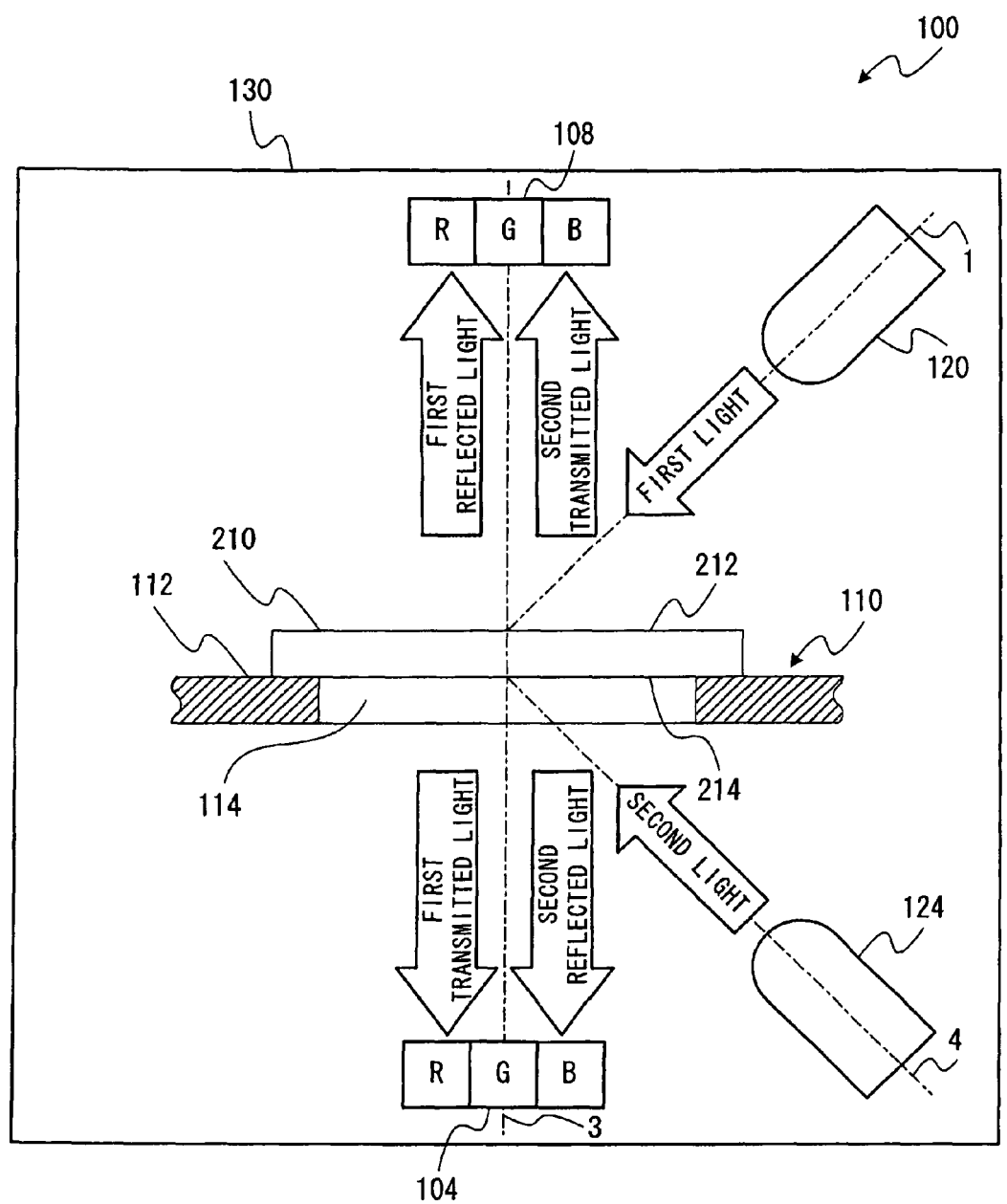
FIG. 16 is another example of the oil state monitoring device shown in FIG. 1.

Colors of the contaminants are explained with FIG. 15. A three dimensional map as shown in FIG. 15 has color points: black (0,0,0), red (255,0,0), green (0.255,0), blue (0,0,255), white (255,255,255), yellow (255,255,0), magenta (255,0,255), and cyan (0,255,255), as the diagram-apexes; and indicates colors of the contaminants in a space of the three dimensional diagram. Colors of the contaminants concentrated in the black, the brown, the gray, and the white. In addition, they were distributed slightly on the red-side to a diagonal line connecting the black color-point and the white color point as the axis, and many of them showed reddish colors. The colors along a parabolic line on the red-side were mainly brownish, and the colors on the diagonal line were mainly black, gray, and white.

The embodiment of the present invention can bring, for example, the below described effects.

(1) The embodiment of the present invention for monitoring oil states employs a configuration where the first transmitted light, which is the first light emitted from the first light sources 120 and 122 which are installed on a side of the first face 212 of the membrane filter 210 and penetrated through the membrane filter 210 after oil content-removal, is detected with the first color sensor 104. In addition, the embodiment of the present invention employs a configuration where the second transmitted light, which is the second light emitted from the second light sources 124 and 126 which are installed on a side of the second face 214 of the membrane filter 210 and penetrated through the membrane filter 210 after oil content-removal, is detected with the second color sensor 108. In other words, the embodiment of the present invention employs elements based on the transmitted light which is light emitted from the light sources and penetrated through the membrane filter 210 after oil content-removal. Specifically, the embodiment of the present invention employs the maximum color differences and $\Delta E_{RGB}$ as parameters for judging (monitoring) the oil degradation states. Such employment makes it possible to judge slight color differences with high sensitivity, even if colors in the section W of the membrane filter 210 after oil content-removal which filtered the oil and captured the contaminants 216 are light. Then, the embodiment of the present invention can judge (monitor) oil degradation states accurately for proper estimation of life expectancy of oil.

(2) The embodiment of the present invention employs a configuration where the first reflected light, which is the first light reflected from the first face 212 of the membrane filter 210 after the oil content removal, is detected with the second color sensor 108, including the foregoing configurations in (1). In addition, the embodiment of the present invention employs a configuration where the second reflected light, which is the second light reflected from the second face 214 of the membrane filter 210 after the oil content removal, is detected with the first color sensor 104. Such employment makes it possible to judge (monitor) states of the contaminants 216 captured in the membrane filter 210 with even higher accuracy; in other words, to judge (monitor) states of the oil degradation without being influenced by a distribution state of the contaminants 216.

(3) The embodiment of the present invention for monitoring oil states has the first light sources 120, 122 and the second light sources 124, 126 emit light with different timing in the third and fourth steps. Such different timing-light emission enables the first color sensor 104 to detect each color component of the first transmitted light produced from the first light and that of the second reflected light produced from the second light, with different timing. In addition, such different timing-light emission also enables the second color sensor 108 to detect each color component of the second transmitted light produced from the second light and that of the first reflected light produced from the first light, with different timing. Such embodiment of the present invention can carry out the color component-detection with high accuracy, distinguishing each color component of the first transmitted light from that of the second reflected light as well as distinguishing each color component of the second transmitted light from that of the first reflected tight. Therefore, the embodiment of the present invention for monitoring the oil states can judge (monitor) the oil degradation states with high accuracy.

(4) The embodiment of the present invention for monitoring oil states employs a configuration where the procedures related to the self-diagnostic-function in S102 is performed prior to the procedures from S104 through S120 explained in FIG. 3 that correspond to the third and fourth steps of the oil state monitoring method. As previously described, the embodiment of the present invention detects the first transmitted light and the second reflected light with the color sensor 104, and the first reflected light and the second transmitted light with the color sensor 108 (S106, S108, S112, S114). Then, predetermined arithmetic processing is carried out, using each color component (the RGB value) detected with the first color sensor 104 and the like (S116, S118), and the oil degradation states are judged (S120).

Performing the procedures of S102 before the above described procedures can achieve the high accuracy judgment (monitoring). In other words, skipping the procedures of S102 produces a variation in luminance or luminous intensity and the like of the first light and the other light emitted from the first light sources 102, 122 and the like. Specifically, each color component detected with the first color sensor 104 and the like can vary even with the same membrane filter 210 after oil content-removal; thus, the stable judgment cannot be achieved.

The embodiment of the present invention may be also provided as follows.

(1) The aforementioned embodiment of the present invention uses the membrane filter 210 as the one for filtering oil. However, a filter which is different from the membrane filter 210 may be used. In other words, a filter for filtering the oil may be the one with net structure which is capable of catching contaminants in oil.

(2) The previously described-embodiment was explained with the oil state monitoring device 100 including the first light sources 120, 122, the first color sensor 104, the second light sources 124, 126, and the second color sensor 108, as an example. However, other configurations may be used for the embodiment. For example, the embodiment may have the oil state monitoring device 100 without the first light source 122 and the second light source 126.

In addition, the embodiment may have the oil state monitoring device 100 without the second light sources 124, 126 and the second color sensor 108. In this case, oil degradation states are judged (monitored) according to the first transmitted light. Moreover, the embodiment may have the oil state monitoring device 100 without the second light sources 124 and 126. In this case, oil degradation states are judged (monitored) according to the first transmitted light or according to the first transmitted light and the first reflected light. Furthermore, the embodiment may have the oil state monitoring device 100 without the second color sensor 108. In this case, oil degradation states are judged (monitored) according to the first transmitted light or according to the first transmitted light and the second reflected light.

Moreover, even if the embodiment employs the oil state monitoring device 100 with the first light sources 120, 122, the first color sensor 104, the second light sources 124, 126, and the second color sensor 108, the configuration may exclude, for example, the first reflected light and the second reflected light from oil degradation state-judgment (monitoring). In other words, oil degradation states may be judged (monitored) according to the first transmitted light and the second transmitted light. In addition, the configuration may exclude the second reflected light from oil degradation state judgment (monitoring). In other words, oil degradation states may be judged (monitored) according to the first transmitted light, the second transmitted light, and the first reflected light. Furthermore, the configuration may exclude the second transmitted light or the second transmitted light and the second reflected light from oil degradation state judgment (monitoring).

The first transmitted light and the second transmitted light both are light that penetrated the membrane filter 210 after oil content-removal; therefore, each color component of the first transmitted light detected with the first color sensor 104 and that of the second transmitted light detected with the second color sensor 108 are basically identical.

(3) The oil state monitoring device 100 may be configured separately from machinery or equipment which uses oil to be monitored. In addition, the oil state monitoring device 100 may be configured being connected to machinery or equipment which uses oil to be monitored. The configuration where the oil state monitoring device 100 is connected to the machinery or equipment may automatically sample a predetermined amount (e.g. 25 ml) of oil used in the machinery from an oil tank of the machinery and the like, and may perform the aforementioned oil state monitoring method (estimation of life expectancy of oil) with predetermined timing. The predetermined timing may be, for example, at machine-starts, at machine-stops, at predetermined time every day, or at predetermined time and on predetermined days every week or every month.

What is claimed is:

1. An oil state monitoring method for monitoring degradation states of oil used in machinery or equipment, the oil state monitoring method comprising:
    a filtering step that filters the oil with a filter;
    a filter treatment step that removes the oil content from the filter which filtered the oil in the filtering step and which captured contaminants which are present in the oil prior to an oil filtration; and
    a transmitted light-detection step that detects color components of transmitted light being light which is emitted onto the filter treated in the filter treatment step and which is penetrated through the filter.

2. The oil state monitoring method according to claim 1, wherein the transmitted light-detection step includes a step of detecting color components of first transmitted light which is first light
    that is emitted from first light source which is set on a side of a first face of the filter which is the side where the oil is present prior to the oil filtering in the filtering step,
    that is emitted onto the filter treated in the filter treatment step, and
    that is penetrated through the filter, on a side of a second face which is a reverse side of the first face.

3. The oil state monitoring method according to claim 2, further comprising:
    a reflected light-detection step that detects, on the side of the first face, color components of first reflected light which is the first light reflected from the first face.

4. The oil state monitoring method according to claim 3, wherein
    the transmitted light-detection step further includes a step of detecting, on the side of the first face, color components of second transmitted light which is second light that is emitted from second light source which is set on the side of the second face, that is emitted onto the filter treated in the filter treatment step, and that is penetrated through the filter, and
    the reflected light-detection step further includes a step of detecting, on the side of the second face, color components of second reflected light which is the second light reflected from the second face.

5. An oil state monitoring device for monitoring oil degradation states with a filter, which filters oil used in machinery or equipment, which captures contaminants which are present in the oil prior to an oil filtration, and which oil content were removed from, the oil state monitoring device comprising:
- a first light source that is installed at least on a side of a first face, which is either side of the filter which is set in the oil state monitoring device, and which is a side where the oil is present prior to the oil filtration at the filtering and that emits first light onto the filter to monitor the oil degradation states;
- a second light source that is installed on the side of a second face which is a reverse side of the first face and that emits second light onto the filter to monitor the oil degradation states;
- a first color sensor that is installed at least on a side of the second face and that detects color components of first transmitted light which is the first light penetrated through the filter and color components of second reflected light which is the second light reflected from the second face; and
- a second color sensor that is installed on the side of the first face and that detects color components of first reflected light which is the first light reflected from the filter and color components of second transmitted light which is the second light penetrated through the filter.

* * * * *